United States Patent

Igushi et al.

[11] Patent Number: 5,922,424
[45] Date of Patent: Jul. 13, 1999

[54] LAMINATING FILM FOR METAL, LAMINATED METAL SHEET AND METAL CONTAINER

[75] Inventors: Hideki Igushi; Hiroshi Nagano; Katsuaki Kuze, all of Inuyama; Tsutomu Isaka, Osaka, all of Japan

[73] Assignee: Toyo Boseki Kabushiki Kaisha, Osaka, Japan

[21] Appl. No.: 08/823,397

[22] Filed: Mar. 24, 1997

[30] Foreign Application Priority Data

Mar. 25, 1996 [JP] Japan .................................... 8-067924
Apr. 8, 1996 [JP] Japan .................................... 8-085159

[51] Int. Cl.⁶ ............................ B32B 15/08; B65D 90/04
[52] U.S. Cl. ........................ 428/35.9; 428/458; 428/480; 428/483; 220/62.11; 220/906
[58] Field of Search ................... 428/35.8, 458, 428/35.9, 480, 483; 220/415, 906, 456, 457, 62.11

[56] References Cited

U.S. PATENT DOCUMENTS

| | | | |
|---|---|---|---|
| 5,137,762 | 8/1992 | Aizawa et al. | 428/358 |
| 5,409,129 | 4/1995 | Tsukada et al. | 220/456 |
| 5,686,510 | 11/1997 | Asai et al. | 428/35.8 |
| 5,700,529 | 12/1997 | Kobayashi et al. | 428/35.8 |
| 5,705,240 | 1/1998 | Machii et al. | 428/35.8 |

FOREIGN PATENT DOCUMENTS 436739  7/1991  European Pat. Off. .

OTHER PUBLICATIONS

Database WPI, Section Ch., Week 9711, Derwent Publications Ltd., London, GB; Class A12, AN 97–112586, XP002034948 & JP 08 325 514A (Mitsui Petrochem Ind. Co., Ltd.), Dec. 10, 1996.
Database WPI, Section Ch., Week 8907, Derwent Publications, Ltd., London, GB; Class A25, AN 89–051328, XP002034949 & JP 64 001 736A (Dainichiseika Color & Chem. Mfg.), Jan. 6, 1989.
Database WPI, Section Ch., Week 7817, Derwent Publications Ltd., London, GB; Class A32, AN 78–30653A, XP002034050 & JP 52 109 537A (*G Gijutsu Kenkyusho KK), Sep. 13, 1977.
Database WPI, Section Ch., Week 9209, Derwent Publications Ltd., London, GB; Class A18, AN 92–068082, XP002034951 & JP 04 010 927A (Toppan Printing Co., Ltd.), Jan. 16, 1992.
Database WPI, Section Ch., Week 9602, Derwent Publications Ltd. London, GB; Class A23, AN 96–016248, XP002034952 & JP 07 290 644A (Mitsui Petrochem. Ind. Co., Ltd.), Nov. 7, 1995.
Database WPI, Section Ch., Week 9602, Derwent Publications Ltd., London, GB; Class A23, AN 96–016247, XP002034953 & JP 07 290 643A (Mitsui Petrochem. Ind. Co., Ltd.), Nov. 7, 1995.
Database WPI, Section Ch., Week 9421, Derwent Publications Ltd., London, GB; Class A23, AN 94–173930, XP002034954 & JP 06 116 486A (Toray Ind. Inc.), Apr. 26, 1994.
Database WPI, Section Ch., Week 9043, Derwent Publications Ltd., London, GB; Class A18, AN 90–325049, XP002034955 & JP 02 233 372 A (Mitsui Fluorochemical Co., Ltd.), Sep. 14, 1990.
Database WPI, Section Ch., Week 9329, Derwent Publications Ltd., London, GB; Class A23, AN 93–232419, XP002034956 & JP 05 155 991A (Teijin Ltd.), Jun. 22, 1993.

*Primary Examiner*—Rena L. Dye
*Attorney, Agent, or Firm*—Kenyon & Kenyon

[57] ABSTRACT

A laminating film for a metal sheet, which comprises a thermoplastic resin and which is free of a pinhole having a diameter of not less than 0.1 mm φ at least in the portion laminated on the metal sheet, a metal sheet prepared by laminating this film, and a metal container formed from this metal sheet. The film of the present invention is superior in corrosion resistance, flavor resistance and printability. Hence, the metal sheet and metal container of the present invention have beautiful appearance and high food protection effect.

7 Claims, 1 Drawing Sheet

LAMINATING FILM FOR METAL, LAMINATED METAL SHEET AND METAL CONTAINER

FIELD OF THE INVENTION

The present invention relates to a laminating film for imparting heat resistance, fine appearance and rust proof to a metal material usable for containers of soft drinks, beer and canned food, a metal sheet laminated with said film and to metal containers produced by forming said laminated metal sheet into a can shape.

BACKGROUND OF THE INVENTION

For inhibiting corrosion of the inner and outer surfaces of metal cans, paints are conventionally applied, wherein used are thermosetting resins.

Other methods include the use of thermoplastic resins. For example, a polyolefin film is laminated on a heated tin-free steel, or a polyester film with good heat resistance is laminated on a metal sheet to be used for cans.

Many thermosetting paints are of solvent type. For forming a coating therefrom, heating at a high temperature for a long time, for example, at 150–250° C. for several minutes, is necessary. In addition, a large amount of organic solvent drifts in the air during baking. Accordingly, improvements with regard to the simplification of steps and prevention of pollution are desired. It is inevitable, moreover, that a small amount of organic solvent remains in the coating when a coating is formed under the above-mentioned conditions, and the remainder of the organic solvent migrates into the food packed in a metal can applied with the coating and degrades taste and smell of the food. Also, additives or low molecular substances which may be produced by an incomplete crosslinking reaction, both being contained in the paint, may move into the food to exert the same adverse influences as in the case of residual organic solvent.

Of the above-mentioned problems, simplification of the steps and prevention of pollution can be achieved by the use of thermoplastic resins. The use of a polyester from among the thermoplastic resin films is most preferable for this end.

That is, a polyester film is superior in heat resistance, so that it does not require additives such as a heat stabilizing agent, and has less amount of low molecular substances. This film is advantageous in dealing with the problems of poor taste and smell of food caused by migration of additives or low molecular substances produced.

When a thermoplastic resin film, which is typically a polyester film, having a pinhole is laminated on a metal sheet and said laminated metal sheet is formed into a metal can, the pinhole in said film causes corrosion of the metal sheet to result, on one hand, in markedly degraded visibility or beautiful design of the trademark printed on the outer surface of the metal can, and, on the other hand, migration of oxide compound (rust) of the metal sheet to the food in the metal can, thus deteriorating taste and smell of the food, or even health of human.

As the materials for various containers of soft drinks, beer, canned food and the like, metal sheets of steel, aluminum and the like have been mainly used. Various printings and colors are applied onto the outer surface thereof to indicate the contents, brand and the like. These containers are colored and printed by such a practical method as, for example, slitting a metal sheet into a predetermined size, printing thereon by offset printing and baking; or slitting and then bending the sheet into a tubular shape, seam welding, printing by offset printing and baking. Subsequent flange processing, inside coating and baking, seam processing and so on produce metal containers.

Whether printing on a flat sheet or a tubular article after tube-forming, a direct printing on a metal material using a metal intaglio as in gravure is not available. This is because metallic materials are so hard that uniform contact of the metal intaglio with the entire printing area is extremely difficult. To overcome this difficulty, an elastic impression such as a rubber impression or flexible resin impression has been conventionally used. Printing sensitivity using such elastic intaglio is poor and clear printing cannot be achieved. In addition, complicated printing involving setting of a wide range of gradation as in half-tone printing and photograph printing is hard to perform, and only very simple printing and coloring have been actually performed.

For a gorgeous three-dimensional printing, a multiple printing using a number of paints is required. This requires an extended time of drying and baking printed inks, and once such multiple printing is incorporated in a can production process, the drying and baking of printed inks become rate-determining steps, which in turn makes the can production speed strikingly slow. The practical number of printings at an industrial scale is naturally limited, and satisfactory visibility and beautiful design cannot be produced by this type of printing.

While there are known methods for offset printing on a slit-processed metal sheet, half-tone printing is still difficult, and the situation stands the same as in the aforementioned gravure, as long as the printed matters do not have satisfactory visibility and beautiful design.

With an aim of solving the above-mentioned problems, a method for laminating a film printed with a trademark design on a metal sheet has been proposed (Japanese Patent Unexamined Publication No. 4-292942).

Generally, a thermoplastic resin film has been laminated on said metal sheet and a cured heat resistant layer is formed to prevent softening and whitening of the thermoplastic resin film due to heat for seam welding during can production and heat treatment or retort treatment after sealing the content in a container. Said cured heat resistant layer also functions to prevent incident of flaw and allows smooth passage of the sheet, in each step of can production. For example, Japanese Patent Unexamined Publication No. 5-11979 teaches that the cured heat resistant layer preferably has a static friction coefficient of not more than 0.2.

An improved slip property of the cured heat resistant layer makes the sheet pass more smoothly and prevents incident of flaw. A single improvement in slip property of the cured heat resistant layer is nevertheless insufficient to prevent flaws. The flaws on the surface of the cured heat resistant layer, which were made during can production step, food packing step and the like, partially degrade visibility of the trademark printed thereon despite the expected benefit afforded by the visibility that the printed film should have, thus failing to satisfy the high demand in the market.

When a thermoplastic resin film having a pinhole is laminated on a metal sheet and metal cans are formed from the obtained laminated metal sheet, moreover, the pinhole in said film causes corrosion of the metallic can material, which in turn vastly impairs visibility of the printed trademark and beautiful design thereof.

It is therefore an object of the present invention to provide a laminating film superior in corrosion resistance, which is devoid of a pinhole and free of the above-mentioned problems. Particularly, the object is to provide a laminating film conducive to the corrosion resistance of metal sheet due to the absence of a pinhole, which is capable of providing a beautiful metal sheet having superior visibility and high quality appearance.

Another object of the present invention is to provide a laminated metal sheet superior in corrosion resistance wherein the film is free of a pinhole.

A still another object of the present invention is to provide a metal container superior in corrosion resistance wherein the film is free of a pinhole.

SUMMARY OF THE INVENTION

According to the present invention, a laminating film for a metal sheet has been provided, which is free of a pinhole having a diameter of not less than 0.1 mm $\phi$ at least in the portion laminated on a metal.

The present invention also provides a laminating film for a metal sheet, which film being a multi-layer film comprising a thermoplastic resin film and a substantially transparent cured heat resistant layer having an abrasion resistance of the surface thereof of not more than 1.2%, which is formed on at least one surface of the thermoplastic resin film.

In the present invention, the number of the above-mentioned pinhole is detected using a high voltage application type pinhole detector.

It is preferable in the present invention that the above-mentioned thermoplastic resin be a polyester resin.

It is preferable that the above-mentioned thermoplastic resin film have a surface tension of not less than 420 $\mu$N on at least one surface thereof and that the film have a shrinkage percentage in the longitudinal direction and transverse direction after heat treatment at 150° C. for 30 minutes of not more than 5% in both directions.

The present invention also relates to a laminated metal sheet wherein the above-mentioned film is laminated on a metal sheet.

The present invention further relates to a metal container formed using the above-mentioned laminated metal sheet.

Figure 1:
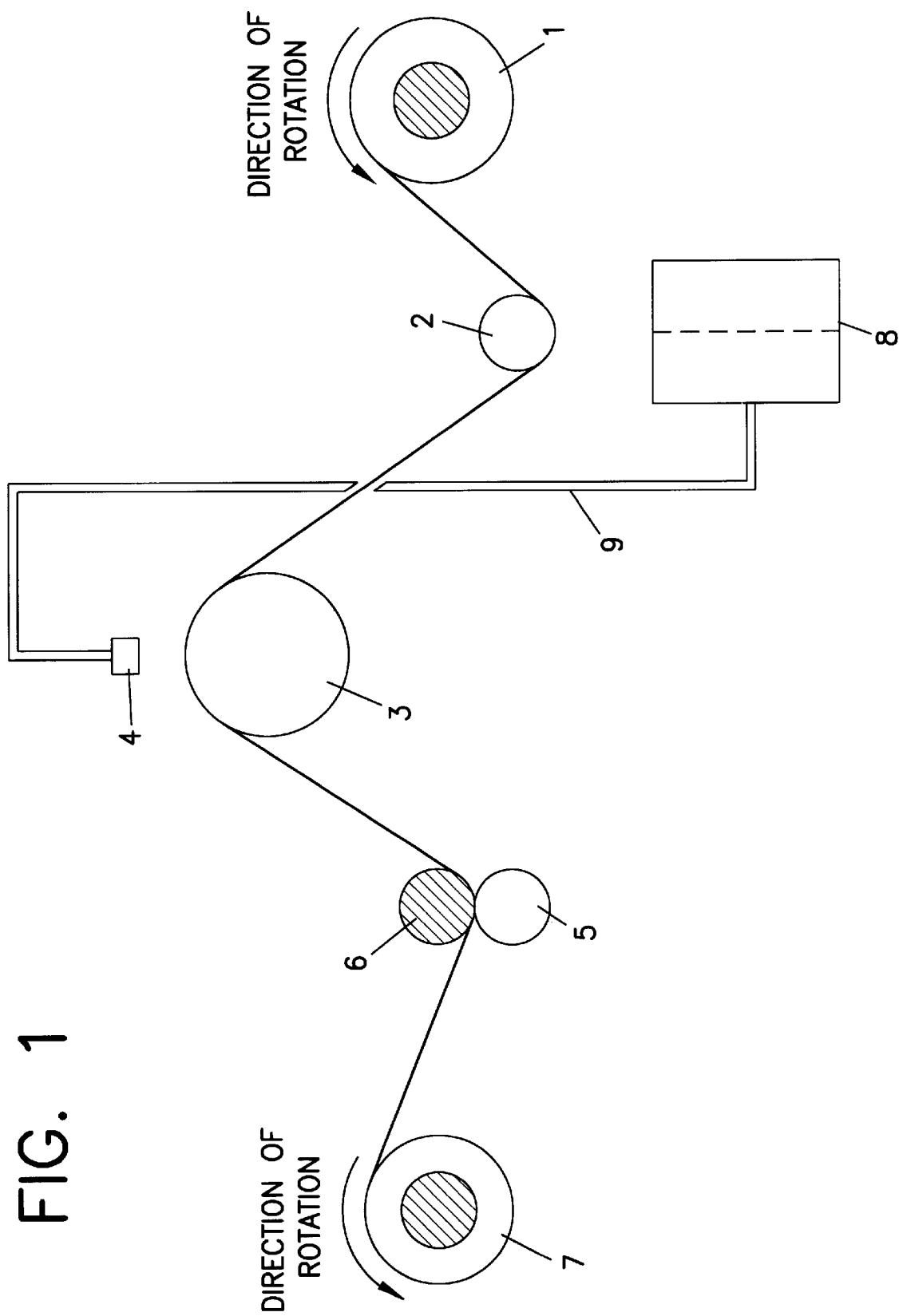
FIG. 1 shows a device for detecting a pinhole in a film and detection method.

In the FIG. 1 is a film prior to pinhole detection test, which is wound on an unrolling shaft, 2 is a guide roller, 3 is a detection roller, 4 is a detection electrode, 5 is a guide roller, 6 is a pressure roller, 7 is a film after pinhole detection test which is wound on a winding shaft, 8 is a high voltage generator and a pinhole detection data processor, and 9 is a cable wire.

DETAILED DESCRIPTION OF THE INVENTION

It has been found that a thermoplastic resin film cannot afford a pinhole having a size of 0.1 mm $\phi$ or above to accomplish the aforementioned objects. In other words, a pinhole having a size of less than 0.1 mm $\phi$ does not impair rust proof property of a metal sheet, since such pinhole present just before lamination can be blocked as a result of, for example, a very small size variation caused by the heat history of the film during heat pressure lamination of the film on a metal sheet, or a slight flow caused by the heat history during lamination of an adhesive and/or an adhesive layer present in between the film and the metal sheet.

It is essential that at least the portion laminated on a metal be devoid of a pinhole having a size of 0.1 mm $\phi$ or above.

In particular, irrespective of the size of the production lot of the film, that is, be it a small lot, medium lot or large lot, the film of one production lot desirably has no pinhole having a diameter of not less than 0.1 mm $\phi$. To be specific, the number of pinhole having a diameter of not less than 0.1 mm $\phi$ is desirably zero, i.e., 0 pinhole/not more than 1,000 m$^2$, 0 pinhole/not more than 10,000 m$^2$, 0 pinhole/not more than 100,000 m$^2$, 0 pinhole/$\infty$ m$^2$.

Pinholes are detected using a detector based on high voltage application. This detector enables detection of every pinhole having a diameter of not less than 0.1 mm $\phi$. A detector capable of detecting every pinhole having a diameter of not less than 0.01 mm $\phi$ is more preferable.

FIG. 1 shows one example of a pinhole detector to be used in the present invention, which is based on high voltage application. A film is unrolled and run toward a guide roller 2 from the film roll attached to an unrolling shaft 1. If a pinhole is contained in the film, a discharge phenomenon occurs at the detection electrode 4 when the film runs between the detection roller 3 and a detection electrode 4 set above the detection roller 3, and said pinhole is detected by a high voltage generator and pinhole detection data processor of 8. Then, the film runs between a guide roller 5 and the pressure roller 6, and wound around the core attached to the winding shaft 7.

While the pinhole detector may be set on-line or off-line with regard to the film production process, preferred is an on-line installment.

A pinhole having a diameter of not less than 0.1 mm $\phi$ can be eliminated by thoroughly drying the starting material of the thermoplastic resin film. For example, when a polyester resin is used as a thermoplastic resin, the water content of the starting material should be set to 50 ppm or below. When it exceeds 50 ppm, air foams are formed in the film during film production and ruptured during passage through various steps to undesirably produce pinholes.

In addition, resin deteriorates and other contaminant components should be thoroughly removed in the resin melting step for forming a thermoplastic resin film. For this end, at least one filter should be used in this step. When a thermoplastic resin film is formed according to a resin melting step without a filter, bubbles grow in the film with contaminant matters as nuclei, which bubbles are ruptured during various steps thereafter to ultimately become undesired pinholes.

Moreover, a thermoplastic resin film should be produced in a clean state devoid of drifting matters which may ride on or attach to the film. When a lot of drifting matters are present during the production of a thermoplastic resin film, airborne foreign matters ride on or attach to said film, and are wound up together with the film in the film winding step and make holes in the film by the action of tension applied when winding the film and/or pressure of welding.

The quality of the film is examined using the pinhole detector to be mentioned later and the product is classified according to the number of the pinholes.

Examples of preferable thermoplastic resin film include films made from polyester resin, polypropylene resin, polymethylpentene-1, polycarbonate, polyimide, PPS, PEK, PEEK and the like and Various modified resins thereof. Of these, a polyester resin film is particularly preferable in view of the balance between the heat resistance and economic aspect. The polyester to be used in the present invention is obtained by condensation polymerization of a polycarboxylic acid and a polyhydric alcohol.

The polycarboxylic acid component includes, for example, dicarboxylic acid such as aromatic dicarboxylic acid (e.g. terephthalic acid, isophthalic acid, phthalic acid, naphthalene dicarboxylic acid, diphenyl dicarboxylic acid), aliphatic dicarboxylic acid (e.g. adipic acid, azelaic acid, sebacic acid, decanedicarboxylic acid, dodecanedicarboxylic acid, dimer acid) and alicyclic dicarboxylic acid (e.g. cyclohexanedicarboxylic acid). Of these, aromatic dicarboxylic acids such as terephthalic acid, isophthalic acid and naphthalene dicarboxylic acid are preferable in terms of protection of contained food and so-called flavor resistance, particularly when said film is applied inside a metal container.

The polyhydric alcohol component includes glycols such as aliphatic diols (e.g. ethylene glycol, diethylene glycol, triethylene glycol, propanediol, butanediol, hexanediol, dodecanemethylene glycol, neopentyl glycol), alicyclic diols (e.g. cyclohexanedimethanol) and aromatic diols (e.g. addition product of bisphenol derivative with ethylene oxide), with preference given to ethylene glycol.

As said polyester, a composition containing polyethylene terephthalate or polyethylene terephthalate containing 0.6–6% by weight (converted to polyether component) of a polyester-polyol block copolymer is particularly preferable. This composition beneficially suppresses whitening of film which is caused by a treatment with hot water, such as a retort treatment.

It is preferable that 70% by mole or more and more preferably 80% by mole or more of ethylene terephthalate units are contained in said polyester.

When the ethylene terephthalate units are not less than 70% by mole, heat resistance does not become poor, so that stretching of a film when laminating same on a metal to form a can, reduction of width and occurrence of wrinkles due to the contraction by heat can be avoided. As a result, laminating conditions do not need to be modified so as to avoid such problems and productivity does not fall. In addition, the cost of the starting material of polyester does not become unbeneficially high.

Said polyester preferably has an intrinsic viscosity of not less than 0.5, more preferably 0.55–0.85, from the aspect of dynamic characteristics.

It is preferable that the thermoplastic resin contain inorganic particles and/or crosslinked polymer particles as appropriate for imparting slip property and scratch resistance during can production, or, when the resin is a polyester, one or more components selected from thermoplastic resins incompatible with the polyester may be added.

The aforesaid components may be used alone or in combination. Preferred is a combined use.

The inorganic fine particles may be any insofar as they are insoluble in polyester and are inert. Specific examples include metal oxides such as silica, alumina, zirconia and titanium oxide, compound oxides such as kaolin, zeolite, sericite and sepiolite, sulfates such as calcium sulfate and barium sulfate, phosphates such as calcium phosphate and zirconium phosphate, and carbonates such as calcium carbonate. These inorganic fine particles may be natural or synthetic and are subject to no particular limitation on particle shape.

The inorganic fine particles may be used alone or in combination. When the inorganic fine particles alone are used, a combination of cohesive amorphous silica or spherical silica and zeolite is preferable.

As the polymer particle, any suffices for use insofar as it stands the temperature of melt-forming the thermoplastic resin. Examples thereof include copolymers of acrylic monomers such as acrylic acid, methacrylic acid, acrylate and methacrylate, styrene monomers such as styrene, alkyl-substituted styrene and the like, and crosslinking monomers such as divinylbenzene, divinylsulfone, ethylene glycol dimethacrylate, trimethylolpropane trimethylacrylate and pentaerythritol tetramethylacrylate; melamine resins; benzoguanamine resins; phenol resins; silicone resins; and the like. Of these, preferred are copolymers of acrylic monomer and/or styrene monomer and crosslinking monomer.

The crosslinking polymer particles may be used alone or in combination.

The method for producing said crosslinking polymer particles is not subject to any particular limitation and conventional emulsion polymerization and suspension polymerization may be used. Pulverization or classification may be done on demand to adjust the particle size and particle distribution of said polymer particles.

Examples of thermoplastic resin incompatible with polyester include polyolefin resins, polystyrene resins, polyacrylic resins, polycarbonate resins, polyamide resins, polysulfone resins and aromatic polyester resins. The thermoplastic resin may be used alone or in combination. In addition, these resins need not be particles.

The above-mentioned inorganic fine particles, crosslinking polymer particles and thermoplastic resin incompatible with polyester may be added to a thermoplastic resin during the manufacturing process of the thermoplastic resin, or a thermoplastic resin and the above-mentioned component may be mixed and melt-kneaded. Alternatively, the above ingredients may be added in a master batch containing them at high concentrations. The preferable content is 0.3–5% by weight of the entire amount of the film components.

The thermoplastic resin may contain antioxidants, heat stabilizers, ultraviolet absorbers, plasticizers, pigments, antistatic agents, lubricants, crystalline nuclei and the like as necessary.

The above-mentioned thermoplastic resin may be produced by any method. In the case of polyester, for example, conventionally known ester exchange, direct polymerization and the like may be used. For a higher molecular weight, solid polymerization may be used.

It is also preferable that said thermoplastic resin film has a wet surface tension as defined by JIS-K-6768 of not less than 420 $\mu$N at least on one surface thereof.

The wet surface tension of not less than 420 $\mu$N can be achieved by any surface treatment such as corona discharge treatment, primer treatment, ozonation, plasma treatment, electrobeam irradiation, frame treatment, chemical treatment and the like. In particular, corona discharge treatment is recommended.

When the wet surface tension is not less than 420 $\mu$N, a strong adhesion between a metal sheet and the film is obtained, thereby preventing peeling off of the film from the metal sheet during or subsequent to can production.

In addition, shrinkage percentage in the longitudinal direction (machine direction) and transverse direction after heat treatment at 150° C. for 30 minutes is preferably not more than 5% in both directions.

The shrinkage percentage may be adjusted to not more than 5% by an optional method. For example, a heat fixing step may be established in the production process of film to relax shrinkage stress of the film, or a film forming rate or film winding rate is set to a level which enables relaxation of stress remaining in the film by minimizing the tension applied onto the film during film forming. In particular, heat fixing is desirable.

When the above-mentioned shrinkage percentage is not more than 5%, a uniformly laminated metal sheet can be advantageously obtained without wrinkles made by heat contraction when laminating with a metal sheet.

Besides the above-mentioned, addition of a heat-resistant overcoat layer, addition of a known additive such as heat stabilizer, and the like are preferable for the added improvement in heat resistance.

When the film is applied to the outer surface of a can, a thermoplastic resin film having suitable degree of flexibility is preferably used to provide visible, beautiful multiple prints and to allow easy bending for can production after lamination. This thermoplastic resin film preferably has a melting point of not less than about 160° C., so that it can stand the heat applied during seam welding for can production, inside coating after can production, boiling treatment after packing the content or retort treatment thereafter. A film having a melting point of not less than about 160° C. is almost free from occurrence of pinholes caused by heating for inside coating, loss of smoothness or gloss of the film due to melting, softening or shrinkage of the film, and occurrence of blister-like irregularities, stress crack, delamination and the like of the film.

From the aspects as noted above, most preferable melting point of the thermoplastic resin film is not less than about 160° C., more preferably not less than about 175° C.

The thermoplastic resin film of the present invention may be either an unoriented film or an oriented film. In the case of an oriented film, it may be uniaxially or biaxially oriented, with preference given to a biaxially oriented film for an improved isotropy.

The method for producing said film is not limited. For example, an oriented film may be prepared by a conventional method such as a T-die method or a tubular method.

This thermoplastic resin film has a thickness of 4–50 μm, more preferably 5–30 μm.

The multi-layer film of the present invention has a substantially transparent cured heat resistant layer formed on at least one surface of the thermoplastic resin film.

The cured heat resistant layer to be used in the present invention is made from a material which is substantially transparent and has a melting point or decomposition temperature of, preferably not less than 250° C., more preferably not less than 300° C., which is exemplified by a curable resin such as silicon, epoxy, melamine, urinary, acrylic, urethane, unsaturated polyester, alkyd, oxazoline resins and various modified resins thereof. These curable reactive resins may be made from a single component, or a combination of two or more components. Preferred is the latter.

Said cured reactive resin layer preferably contains a lubricant such as silicone compound, fluorine compound, various wax having a higher hydrocarbon chain and the like, for an improved slip property of the surface of the cured heat resistant layer. Organic or inorganic fine particles may be preferably contained for the same purpose.

The thickness of the cured heat resistant layer is 0.3–10 g/m$^2$, preferably 0.3–5 g/m$^2$. When it is too thin, the surface cannot be protected sufficiently, and when it is too thick, cracks tend to occur in the cured heat resistant layer during bending process.

In the present invention, for an enhanced visibility of the printed trademark and beautiful design thereof, the surface opposite from the above-mentioned side of the cured heat resistant layer is preferably printed. For this end, the above-mentioned cured heat resistant layer needs to be substantially transparent. Hence, the lubricants and fine particles to be added to the materials constituting the afore-said cured heat resistant layer should be those which do not lower the transparency of the layer; the contents thereof also need careful adjustments.

According to the present invention, the abrasion resistance of the surface of the cured heat resistant layer to be determined by the method to be described later is preferably not more than 1.2%, more preferably not more than 1.0%, and most preferably not more than 0.8%.

When the abrasion resistance is not more than 1.2%, flaws do not tend to occur on the surface of the cured heat resistant layer during can production and packing of food, thereby desirably improving the visibility of the printed trademark and product value.

A method for setting the abrasion resistance to not more than 1.2% is not particularly limited. Inasmuch as the abrasion resistance is affected by the composition and curability of the material constituting the cured heat resistant layer, it is preferable that these factors be considered carefully. The thickness of the cured heat resistant layer is also an important factor.

The cured heat resistant layer is formed by any method. Preferred is a coating method wherein a curable resin is dissolved in a solvent, coated on a thermoplastic resin film and dry-cured. The curing reaction is not particularly limited, and heat, electron beam, ultraviolet light, X ray and other energy sources may be used. From the economic aspect, heat or electron beam is preferably used.

When the cured heat resistant layer is obtained by the coating method wherein the layer is cured by heat, the drying conditions and curing conditions are important factors which vary abrasion resistance. When abrasion resistance is to be adjusted to not more than 1.2%, those conditions should be controlled as appropriate. When the above method is employed, a two-step heating method having drying step and curing step is preferable. The curing step requires high temperature and efficient heating, which are preferably met by infrared heating. The temperature employed for each step of the two-step heating varies depending on the composition of curable resin, the length of oven used for drying or curing step and the like. As a generality, the film is preferably dried at 140° C. or below and cured at 140° C. or above.

For a uniform cured layer to be obtained, the kind of solvent used for preparing coating composition and the content of the residual solvent before the curing step are important.

The laminated metal sheet of the present invention is produced by laminating the aforementioned laminating film on a metal sheet. In the case of lamination of a multi-layer film comprising one cured heat resistant layer, the thermoplastic resin layer is brought into direct contact with the metal. The usable metal sheet includes tin, tin-free steel, aluminum and the like.

The laminating film may be laminated on the metal sheet by any method such as conventional dry laminating or thermal laminating. For example, an adhesive layer is formed on a film and the adhesive side of the film is laminated on a metal sheet. The adhesive layer is preferably formed on the film in a partially cured state and allowed to completely cure while being laminated on the metal sheet. The adhesive may be cured by the use of heat, light or electron beam. It is preferable to use curable resins as long as they strongly adhere to a metal sheet and do not lose adhesion after seam welding for can production or boiling treatment and retort treatment thereafter. Such resin may be epoxy resin, polyurethane resin, polyester resin, polyester polyurethane resin, isocyanate resin or modified resins of these resins.

Another method includes co-extruding a multi-layer film wherein a low melting point polyester resin is laminated as a top surface of the film, and thermally laminating same by heating by energizing the metal sheet. This thermal laminating method is more preferable.

The film may be laminated on either side or both sides of the metal sheet. When a both-side laminating is desired, a simultaneous laminating or sequential laminating may be conducted.

The metal container of the present invention is obtained by forming the above-mentioned laminated metal sheet. The method for forming the metal container is not particularly limited. While the shape of the metal container is not limited, a so-called three-piece can which is preferable for packing retort food, coffee drinks or the like is preferred, wherein the lids of head and ail are seamed to seal the content.

When the laminating film thus obtained is laminated on a metal sheet, the laminated metal sheet comes to have fine appearance and superior abrasion resistance of the surface. The laminated metal sheet can be used as it is as various panels and beautiful outer sheets. When a can having an outer surface laminated with said film is produced by a conventional method, a metal container having extremely fine appearance and design can be obtained.

EXAMPLES

The present invention is described in more detail by way of illustrative examples. It should be noted that the present invention is not limited to the following examples, but can be practiced after modification within the technical scope of the present invention, to the extent that does not deviate from the above-mentioned spirit of the present invention.

In the following examples, "part" means part by weight and "%" means % by weight unless otherwise specified. Each determination followed the method noted below.

(1) Detection of pinhole (by high voltage application)

When pinholes of 0.1 mm ϕ are to be detected, pinholes of this size are formed in a film. Using this film, the distance between the detection electrode 4 and detection roller 3 of the apparatus of FIG. 1 and the voltage to be applied are suitably determined.

In the case of the present Examples, the distance between the detection electrode and detection roller was set to 0.2 mm, the voltage to be applied to 2.4 kV and running rate to 50 m/min. A film sample roll (1000 mm wide, 1000 m long) was run under these conditions and subjected to detection.

(2) Preparation of laminated metal sheet (laminated steel sheet)

The surface of a laminating film to be laminated on a metal was subjected to corona discharge treatment and an adhesive (a mixture of polyurethane adhesive "ADCOTE" manufactured by Toyo Ink Manufacturing Co., Ltd., and a curing agent) was applied to said corona surface by 4 g/m$^2$ (proportion when converted to solid content). The film was dried and aged at 40° C. for 24 hours.

This film was laminated on a degreased cold drawn steel sheet by a thermal laminating method to give a laminated steel sheet.

(3) Rust proof test

A laminating film was subjected to the test of (1) and used to prepare a laminated metal sheet according to the method (2). The sheet was processed into a metal container (can) in a can-forming step. A 1% aqueous solution of NaCl was filled in the can and occurrence of rust and appearance of the can were observed one month later.

(4) Wet surface tension test

A test was run according to JIS-K-6768 to determine the wet surface tension of the film surface to be laminated on a metal sheet.

(5) Heat shrinkage

The shrinkage percentage in the longitudinal direction (MD direction) and transverse direction (TD direction) by heating a film to be laminated on a metal sheet was determined according to JIS-C-2318.

(6) Evaluation of abrasion resistance

A sample film was attached to and fixed on a cross grain cover of corrugated cardboard (defined in JIS-Z-1516, corrugated fiberboard TYPE 3) with a cellophane tape, with a cured heat resistant layer facing up. Sixteen sheets of gauze were superimposed and fixed on a spherical head of a two pound weight hammer. The gauze portion of the hammer was immersed in methyl ethyl ketone for 10 seconds. After immersion, methyl ethyl ketone was allowed to drop naturally. The hammer was swung twice in the perpendicular direction to swing off an excess methyl ethyl ketone.

The two pound weight hammer was reciprocated 100 times over the distance of 160 mm at a rate of 2 seconds/reciprocation on the surface of the sample fixed on the corrugated cardboard.

The load was only the weight of the hammer, and the force was used only to reciprocate the hammer. The gauze was changed every time.

The degree of flaw on the portion of the sample where the hammer was reciprocated was determined by measuring the haze of the film. That is, the difference between the haze (%) of the part under reciprocation and the part which was not was taken as abrasion resistance.

The haze (%) was determined by a haze meter (TOYO SEIKI SEISAKUSHO, LTD.) with respect to an area of 6 mm ϕ. The determination point was changed and determination was repeated 20 times. The average of the 20 determinations was used to express the haze (%).

(7) Static abrasion coefficient of film

The static abrasion coefficient between two surfaces of cured heat resistant layer was determined according to ASTM-D-1894.

Example 1

A mixture of polyethylene terephthalate (97 parts) having an intrinsic viscosity of 0.70 and containing cohesive silica (average particle size 1.5 μm, 0.1%) and polymethyl methacrylate particles (spherical; average particle size 3.0 μm, 1.0%) crosslinked with trimethylol propanetrimethacrylate, and polyethylene terephthalatepolytetramethylene glycol ether block copolymer (3 parts) was adjusted to have a water content of 30 ppm by drying in vacuo and melt-extruded by T-die method to give an amorphous sheet. On this occasion, a two-step melt filter (pore sizes 20 μm and 10 μm) was used in the resin melting step.

Then, the above-mentioned sheet was drawn 3.5 times in the longitudinal direction and 3.5 times in the transverse direction at 90° C. and thermally fixed at 200° C. The both surfaces of the film were subjected to corona discharge treatment to give a 12 μm thick polyester film.

The film was subjected to the test (1) above and the proportion of the detected pinholes having a diameter of 0.1 mm ϕ or above was 0/20,000 m$^2$.

According to the method (2) above, this polyester film was laminated on both sides of the steel sheet. The obtained sheet was subjected to the test (3) with regard to occurrence of rust. The properties thereof are shown in Table 1.

The film for laminating on a metal sheet, laminated sheet and metal container obtained showed superior corrosion resistance with the proportion of rusted cans being 0/1,000,000 cans. Every can maintained superior appearance and the product value of the film was high.

Comparative Example 1

In the same manner as in Example 1 except that a polyester film was used which was obtained using a two-step melt filter having pore sizes of 80 μm and 60 μm in a resin melting step and which contained 0.2 mm φ diameter pinholes at a proportion of one per 1,000 m², a laminated steel sheet was obtained, which was subjected to a test with regard to the incident of rust. The properties of the film and laminated steel sheet are shown in Table 1.

The proportion of the rusted can was one per 50,000 cans. The can evaluated as defective was confirmed to have pinholes. To conclude, said film caused rust in the laminated metal sheet due to the presence of pinholes to ultimately degrade its appearance, and the product value of the film was low.

Comparative Example 2

In the same manner as in Example 1 except that a polyester film was used which was obtained using a two-step melt filter having pore sizes of 100 μm and 80 μm in a resin melting step and which contained 0.3 mm φ diameter pinholes at a proportion of 5 per 1,000 m², a laminated steel sheet was obtained, which was subjected to a test with regard to the incident of rust. The properties thereof are shown in Table 1.

The proportion of the rusted cans was 4 per 50,000 cans. The cans evaluated as defective were confirmed to have pinholes. To conclude, said film caused rust in the laminated metal sheet due to the presence of pinholes to ultimately degrade its appearance, and the product value of the film was low.

Comparative Example 3

In the same manner as in Example 1 except that a polyester film was used which was obtained from a polyester resin mixture having a water content of 500 ppm and which contained 0.2 mm φ diameter pinholes at a proportion of 10 per 1,000 m², a laminate steel sheet was obtained, which was subjected to a test with regard to the incident of rust. The properties thereof are shown in Table 1.

The proportion of the rusted can was 9 per 50,000 cans. The cans evaluated as defective were confirmed to have pinholes. To conclude, said film caused rust in the laminated metal sheet due to the presence of pinholes to ultimately degrade its appearance, and the product value of the film was low.

Comparative Example 4

In the same manner as in Comparative Example 1 except that corona discharge treatment was not applied and a polyester film having a wet surface tension of 380 μN was used, a laminate steel sheet was obtained. The properties thereof are shown in Table 1.

The film for laminating with a metal sheet and laminated sheet obtained had pinholes and the film came off from the metal sheet during can production step, thus indicating low practical use.

Comparative Example 5

In the same manner as in Comparative Example 1 except that heat fixing temperature was set to 135° C. and a polyester film having a shrinkage percentage in the TD direction of 8% was used, a laminated steel sheet was obtained. The properties thereof are shown in Table 1.

The film for laminating with a metal sheet and laminated steel sheet obtained had pinholes and wrinkles that occurred during lamination step, thus indicating low practical use.

The results of Example 1 and Comparative Examples 1–5 are shown in Table 1.

TABLE 1

| | thermo-plastic resin film | water content of thermo-plastic resin | melt filter pore size (two step) | wet surface tension | shrinkage percentage by heating (length-width) | number of detected pinhole (pinhole diameter) | rust proof test results (number of rusted can) |
|---|---|---|---|---|---|---|---|
| Ex. 1 | polyester | 30 ppm | 20 μm–10 μm | 450 μN | 2%–1% | 0/20,000 m² (0.1 mm φ or above) | 0/1,000,000 cans |
| Com.Ex.1 | polyester | 30 ppm | 80 μm–60 μm | 450 μN | 2%–1% | 1/1,000 m² (0.2 mm φ) | 1/50,000 cans |
| Com.Ex.2 | polyester | 30 ppm | 100 μm–80 μm | 450 μN | 2%–1% | 5/1,000 m² (0.3 mm φ) | 4/50,000 cans |
| Com.Ex.3 | polyester | 500 ppm | 20 μm–10 μm | 450 μN | 2%–1% | 10/1,000 m² (0.2 mm φ) | 9/50,000 cans |
| Com.Ex.4 | polyester | 30 ppm | 20 μm–10 μm | 380 μN | 2%–1% | 1/1,000 m² (0.2 mm φ) | — |
| Com.Ex.5 | polyester | 30 ppm | 20 μm–10 μm | 450 μN | 2%–8% | 1/1,000 m² (0.2 mm φ) | — |

Example 2

A sample having 0.05 mm diameter pinhole at a proportion of one per can was subjected to rust proof test (3). As a result, it did not rust one month later. The result indicates that the sample was free of marked degradation of appearance due to rust and had high product value.

Comparative Example 6

A sample having 0.1 mm diameter pinhole at a proportion of one per can was subjected to rust proof test (3). As a result, it rusted one month later, and the appearance was markedly degraded by the rust. Thus, the product value was low.

Comparative Example 7

A sample having 0.2 mm diameter pinhole at a proportion of one per can was subjected to rust proof test (3). As a result, it rusted one month later, and the appearance was markedly degraded by the rust. Thus, the product value was low.

Example 3

Polyethylene terephthalate having an intrinsic viscosity of 0.80 and glass transition temperature of 65° C., and polyethylene terephthalate-polytetramethylene glycol ether block copolymer were added in a proportion such that their content as a polytetramethylene glycol ether component became 4% by weight, and a 12 μm thick polyester film (shrinkage stress at 200° C.: 0.5 kg/mm$^2$) was obtained by film forming and biaxial orientation. A cured heat resistant resin composition comprising bisphenol A epoxy resin (50 parts), polyester resin (35 parts), hexamethoxymethylol melamine (15 parts), silicone resin (1 part), p-toluenesulfonic acid (0.7 part), polyethylene wax (0.2 part) and fluororesin (0.2 part) was dissolved in a solvent mainly containing methyl ethyl ketone/ethyl acetate/toluene, and the coating solution thus obtained was applied onto one side of the film to a thickness after drying of 1 g/m$^2$ by gravure roll. A cured heat resistant layer treated at a drying temperature of 95° C. and curing temperature of 180° C. was laminated to give a laminating film. Hot air was used for drying, and the film was heated by infrared irradiation for curing. The residual solvent content after drying was 100 ppm. The side opposite from the cured heat resistant layer was subjected to corona treatment.

Abrasion resistance and static abrasion coefficient of the laminating film were 0.1% and 0.11, respectively. The number of detected pinholes having a diameter of 0.1 mm φ or more was 0 per 20,000 m$^2$. The multi-layer film obtained was superior in slip property and abrasion resistance without pinholes.

The corona-treated surface of said laminating film was printed and an adhesive was coated on said printed film according to the method (2), which was followed by drying and aging at 40° C. for 24 hours to give a laminating film. Then, this film was laminated on a degreased cold drawn steel sheet by a thermal laminating method to give a laminated steel sheet.

A metal container for soft drinks was prepared from this laminated steel sheet by a conventional method. The laminate surface of the container body thus obtained was clear and beautiful with rich gloss.

Note that, in the above-mentioned container production step, a heat of 270° C. or above was applied to the film and the polyethylene terephthalate layer of the film should have been somewhat softened. As long as the film was protected by cured heat resistant layer of-epoxy modified urea resin, the film was almost free of shrinkage, loss of gloss or denaturing of printed ink layer. This container was treated with boiling water at 100° C. and steam at 125° C. As a result, the laminating film did not whiten or was not deteriorated by heat, but maintained beautiful appearance.

No flaw was made on the surface of the laminating film when each laminated steel sheet was transported during can production or when cans were brought into contact with each other during can production or packing of food. The film had highly visible, beautiful appearance with rich gloss. Thus, the film was highly practical.

This laminating film underwent testing with regard to the rusting according to the method of (3). As a result, the number of rusted can was 0/1,000,000 cans. Every can maintained superior appearance and the product value of the film was high.

Example 4

In the same manner as in Example 3 except that drying temperature was 80° C. and curing temperature was 135° C., a laminating film was obtained. The content of the residual solvent after drying was 600 ppm. Abrasion resistance and static abrasion coefficient of the laminating film were 1.5% and 0.11, respectively. The number of detected pinholes having a diameter of 0.1 mm φ or more was 0 per 20,000 m$^2$. The laminating film obtained was superior in slip property and did not have any pinholes, but inferior in abrasion resistance.

Using this laminating film, a laminated steel sheet and metal container were obtained in the same manner as in Example 3. The laminated sheet and metal container obtained were inferior in abrasion resistance of the surface of the cured heat resistant layer of the laminating film.

Comparative Example 8

In the same manner as in Example 3 except that a film having 1 per 1,000 m$^2$ detected pinhole having a diameter of 0.1 mm φ or more was used, a laminating film was obtained, using which a metal sheet and metal container were prepared. The number of rusted can was 1 per 50,000 cans. The can evaluated as defective was confirmed to have pinholes. To conclude, said film caused rust in the laminated metal sheet due to the presence of pinholes to ultimately degrade its appearance, and the product value of the film was low.

Comparative Example 9

In the same manner as in Example 3 except that a film having 5 per 1,000 m$^2$ detected pinholes having a diameter of 0.1 mm φ or more was used, a laminating film was obtained, using which a metal sheet and metal container were prepared. The number of rusted cans was 4 per 50,000 cans. The cans evaluated as defective were confirmed to have pinholes. To conclude, said film caused rust in the laminated metal sheet due to the presence of pinholes to ultimately degrade its appearance, and the product value of the film was low.

Example 5

In the same manner as in Example 3 except that curing temperature was 170° C., a laminating film was obtained.

Abrasion resistance and static abrasion coefficient of the laminating film were 0.30% and 0.10, respectively.

The number of detected pinholes having a diameter of 0.1 mm φ or more was 0 per 20,000 m$^2$.

Using this laminating film, a laminated steel sheet and metal container were obtained in the same manner as in Example 3. The laminated sheet and metal container obtained were superior in abrasion resistance of the surface of the cured heat resistant layer of the laminating film. The number of rusted cans was 0 per 1,000,000 cans. The cans had high practicality as in Example 3.

Example 6

In the same manner as in Example 3 except that the cured heat resistant resin composition was changed to a composition comprising bisphenol A epoxy resin (70 parts), hexamethoxymethylol melamine (30 parts), p-toluenesulfonic acid (0.10 part), higher fatty acid wax (0.1 part), fluororesin (0.4 part) and silicone resin (1.2 parts), and the drying temperature was 80° C. and the curing temperature was 165° C., a laminating film was obtained.

The content of the residual solvent after drying was 155 ppm. Abrasion resistance index and static abrasion coefficient of the laminating film were 0.22% and 0.09, respectively.

The number of detected pinholes having a diameter of 0.1 mm φ or more was 0 per 20,000 m².

Using this laminating film, a laminated metal sheet and metal container were prepared in the same manner as in Example 3. The abrasion resistance of the surface of the cured heat resistant layer of the laminating film was superior. The number of rusted can was 0 per 1,000,000 cans. They had high practicality as in Example 3.

Example 7

In the same manner as in Example 6 except that the drying temperature was 80° C. and the curing temperature was 135° C. (hot air heating), a laminating film was obtained. The abrasion resistance and static abrasion coefficient of the obtained laminating film were 1.7% and 0.09, respectively. The number of detected pinholes having a diameter of 0.1 mm φ or more was 0 per 20,000 m². The laminating film obtained was superior in slip property and did not have any pinholes, but inferior in abrasion resistance.

Using this laminating film, a laminated metal sheet and metal container were prepared in the same manner as in Example 3. The abrasion resistance of the surface of the cured heat resistant layer of the laminating film was inferior.

The film for laminating with a metal sheet, a metal sheet laminated with this film and metal container obtained from this metal sheet of the present invention are capable of providing a beautiful metal container extremely superior in design and protection of food, which is free of noticeable degradation of appearance and loss of beautiful design due to the occurrence of rust on the metal can or denaturing of food due to the migration of rust components to the food. Consequently, they can be preferably used as metal materials for containers of soft drinks, beer, canned food and the like. In particular, the laminating film having a cured heat resistant layer formed on a thermoplastic resin film is superior in abrasion resistance of the surface of the cured heat resistant layer and corrosion resistance of metal can, and can provide a beautiful metal sheet and metal containers having high gloss and excellent scratch resistance, and free of poor appearance due to the occurrence of rust.

This application is based on application Nos. 67924/1996 and 85159/1996 filed in Japan, the contents of which are incorporated hereinto by reference.

What is claimed is:

1. A multi-layer laminating film for a metal sheet, which comprises a thermoplastic resin film which is free of a pinhole having a diameter of not less than 0.1 mm φ at least in the portion laminated on the metal sheet, and which further comprises a substantially transparent cured heat resistant layer having an abrasion resistance of the surface of not more than 1.2%, which is formed on at least one side of the thermoplastic resin film.

2. The laminating film of claim 1, wherein the thermoplastic resin is a polyester resin.

3. The laminating film of claim 1, wherein the film has a wet surface tension of not less than 420 μN at least on one side thereof.

4. The laminating film of claim 1, wherein the film has a shrinkage percentage after heat treating the film at 150° C. for 30 minutes of not more than 5% in the longitudinal direction and transverse direction of the film.

5. The laminating film of claim 1, which is prepared from a material having a water content of not more than 50 ppm.

6. A metal sheet laminated with a multi-layer film which comprises a thermoplastic resin film, which is free of a pinhole having a diameter of not less than 0.1 mm φ, and which further comprises a substantially transparent cured heat resistant layer having an abrasion resistance of the surface thereof of not more than 1.2%, which is formed on at least one side of the thermoplastic resin film.

7. A metal container formed from a metal sheet laminated with a multi-layer film which comprises a thermoplastic resin film, which is free of a pinhole having a diameter of not less than 0.1 mm φ, and which further comprises a substantially transparent cured heat resistant layer having an abrasion resistance of the surface thereof of not more than 1.2%, which is formed on at least one side of the thermoplastic resin film.

\* \* \* \* \*